United States Patent
Salameh

(10) Patent No.: US 7,146,848 B2
(45) Date of Patent: Dec. 12, 2006

(54) TESTING DEVICE FOR SEAL BODIES

(75) Inventor: Ralf Salameh, Gondelsheim (DE)

(73) Assignee: Federal-Mogul Holding Deutschland GmbH, Burscheid (DE)

(*) Notice: Subject to any disclaimer, the term of this patent is extended or adjusted under 35 U.S.C. 154(b) by 0 days.

(21) Appl. No.: 11/184,335

(22) Filed: Jul. 19, 2005

(65) Prior Publication Data

US 2006/0032292 A1    Feb. 16, 2006

(30) Foreign Application Priority Data

Jul. 20, 2004 (DE) ................... 10 2004 035 111

(51) Int. Cl.
  *G01N 15/08* (2006.01)
(52) U.S. Cl. .......................... 73/38; 73/49.8
(58) Field of Classification Search ................ 73/49.8, 73/38
  See application file for complete search history.

(56) References Cited

U.S. PATENT DOCUMENTS

| | | | | |
|---|---|---|---|---|
| 4,047,422 | A * | 9/1977 | Lyssy ............................. | 73/38 |
| 4,170,895 | A * | 10/1979 | Kliger ........................ | 73/64.47 |
| 4,468,951 | A | 9/1984 | Garcia et al. | |
| 5,375,453 | A | 12/1994 | Rudd et al. | |
| 5,408,168 | A * | 4/1995 | Pfandler ..................... | 318/642 |
| 6,335,202 | B1 * | 1/2002 | Lee et al. .................... | 436/161 |
| 6,467,335 | B1 * | 10/2002 | Mizobe .......................... | 73/38 |
| 6,779,384 | B1 * | 8/2004 | Chun .......................... | 73/64.47 |
| 2004/0040372 | A1 * | 3/2004 | Plester et al. .................. | 73/38 |
| 2005/0223777 | A1 * | 10/2005 | Jensen et al. .................. | 73/38 |

FOREIGN PATENT DOCUMENTS

| | | | |
|---|---|---|---|
| EP | 1084960 A1 | * | 3/2001 |
| EP | 1 384 985 A1 | | 1/2004 |
| GB | 2 345 144 A | | 6/2000 |

OTHER PUBLICATIONS

"A method for determining the permeability and solubility of sulfur in poly (dimethylsiloxane) (RTV)", G. DiGiacomo, E. Spaulding, IBM Corporation, Journal of Applied Polymer Science; vol. 23, pp. 261-274, (1979) http://www3.interscience.wiley.com/cgi-bin/fulltext/104024915/PDFSTART (accessed Jul. 21, 2006).*

* cited by examiner

Primary Examiner—Hezron Williams
Assistant Examiner—Samir M. Shah
(74) Attorney, Agent, or Firm—Robert L. Stearns; Dickinson Wright, PLLC

(57) ABSTRACT

A device for measuring the permeability of fluids and/or vapors through elastomeric seal bodies comprising a container incorporating a recess for holding a test medium, the recess being covered and closed off by a lid by way of screws fastening the lid to said container, wherein the seal body is positionable between the end face of the container and the face of the lid, both surfaces being places so as to face each other, and lockable in position by way of screws using a predetermined load force, and the test medium is measurable as it passes to the exterior through the remaining material thickness of the seal body through a seal gap between the front faces.

20 Claims, 2 Drawing Sheets

TESTING DEVICE FOR SEAL BODIES

This invention claims priority German Patent Application No. 10 2004 035 111.2, filed Jul. 20, 2004.

BACKGROUND OF THE INVENTION

1. Technical Field

The invention relates to a device for testing the permeability of fluids and/or vapors through elastomeric seal bodies.

2. Related Art

As a consequence of new legislation, the permeation of substances through sealing systems has become an important consideration when developing new seal bodies. This applies not only to all the sealing zones in the motor area, for example in respect to fuel permeation, but also to the development of new systems such as fuel cells (hydrogen permeation). In the area of sealing technology permeation rates are currently measured mainly on material samples or by testing complete systems such as tank systems. Usually, a measuring chamber only allows one single sample to be analyzed at any one time. To obtain meaningful permeation data, measurements need to be performed over longer time periods, thereby maintaining the measuring devices occupied with a single analysis for a long time.

The VDA guideline 675245 (Elastomeric components in motor vehicles—Test procedures for determining characteristics: permeability of fluids and vapors through elastomers) describes a test device to measure permeation through material samples using a simple setup (cup test). In this test small containers are first filled with a test medium (e.g. regular fuel mixture). The disk shaped material sample is then introduced into a recess provided on the container. A lid facing the container and providing a screwed connection to it includes a recess on the side of the sample to incorporate a support filter screen aimed at absorbing the internal pressure on the sample, if the test is carried out at elevated temperatures. The lid is provided with a passage allowing the test medium to pass through. The procedure begins with the registration of the initial weight of the container, including its content. If the fluid or the vapor-air mixture escape through the material sample, a reduction of the starting weight will be registered. The weight difference is a direct function of the amount escaped through permeation. The VDA guideline deals exclusively with material samples with a thickness of 2+/−0.1 mm, which is not consistent with the real operating conditions of the respective seal body. The recess provided on the container for holding the material sample is 1.5 mm deep, meaning that the material sample needs to be compressed by 25% by tightening the planar face of the container and the planar face of the lid against each respective side of the material sample. The extent to which the fluid or vapor-air mixture passes through the sample depends on the size of the passage on the lid—which does not correlate with real operating conditions—and the measured value will therefore not apply to a seal body under real installation conditions.

SUMMARY OF THE INVENTION

It is therefore an object of the present invention to provide an improved device for measuring the permeability of fluids and/or vapors that will overcome the disadvantages of the state of the art by providing a measurement in correspondence with real applications, thus providing a basis for the development of new sealing systems for individual seal concepts.

This object and others become apparent as the specification progresses are accomplished by the invention, according to which a device for measuring the permeability of fluids and/or vapors through elastomeric seal bodies comprising a container incorporating a recess for holding a test medium, the recess being covered and closed off by a lid by way of screws fastening the lid to the said container, wherein the seal body is positionable between the end face of the container and the face of the lid, both surfaces being placed so as to face each other, and lockable in position by way of screws using a predetermined load force, and the test medium is measurable as it passes to the exterior through the remaining material thickness of the seal body through a seal gap between the surfaces.

Contrary to prior art in accordance with applicable VDA guidelines, this invention does not use any type of material samples with predetermined thicknesses but, instead, incorporates seal bodies which are intended for real applications between the end face of the container and the face of the lid. With the present invention it is possible to test seal bodies of any shape by adapting the corresponding end face of the container and/or the face of the lid to the individual application conditions. This applies in particular to the contour and roughness of the individual surface.

The standardized cup test, which can only compare material samples, provides a basis for the device presented in this invention, which provides a means of comparing different types of seal bodies (material+design). The device presented here also performs an analysis based on the qualitative measurement of the weight loss of the test medium. According to the present invention the proposed device deviates from the state of the art in that it tests the real seal concept with all the required influencing factors. The escape of the test medium must take place, as is the case in real applications, through the surface of the seal body in direct contact with the face(s) of the container/lid as well as the sealing material itself. The possibility exists to adjust a specific seal gap between the opposing faces in order to represent real tolerance conditions.

The test setup can take place at defined temperature conditions by placing the device in temperature chambers. The seal bodies used in the device presented in this invention are locked in place—as mentioned above—in devices adapted therefore or need to be specially fabricated. If the seal body is provided with seal lips, it is important to ensure that the effective diameter of the seal lips is identical for different test bodies in order to compare different concepts.

The devices are advantageously constructed in aluminum to avoid any permeation through the device itself. By using different materials for the container (e.g. synthetic materials instead of aluminum) it is possible to evaluate the influence of the system components' materials.

The device according to this invention provides the following advantages:

very simple test setup, enabling parallel comparative testing using several devices the device can be exposed to high or low temperatures using simple means it is possible to run so-called temperature profiles the seal gap can be modified to test different pressurization states of the seal body (simulation of system tolerances)

it is possible to modify the faces of the container and the lid (surface structure and roughness)

it is possible to modify the construction materials of the device to assess further system influences.

THE DRAWINGS

The present invention is shown by means of an exemplary embodiment in the appended drawings in which:

FIGS. 1a to 1c show seal bodies 1, 1', 1" of different configurations.

DETAILED DESCRIPTION

Figure 1A:
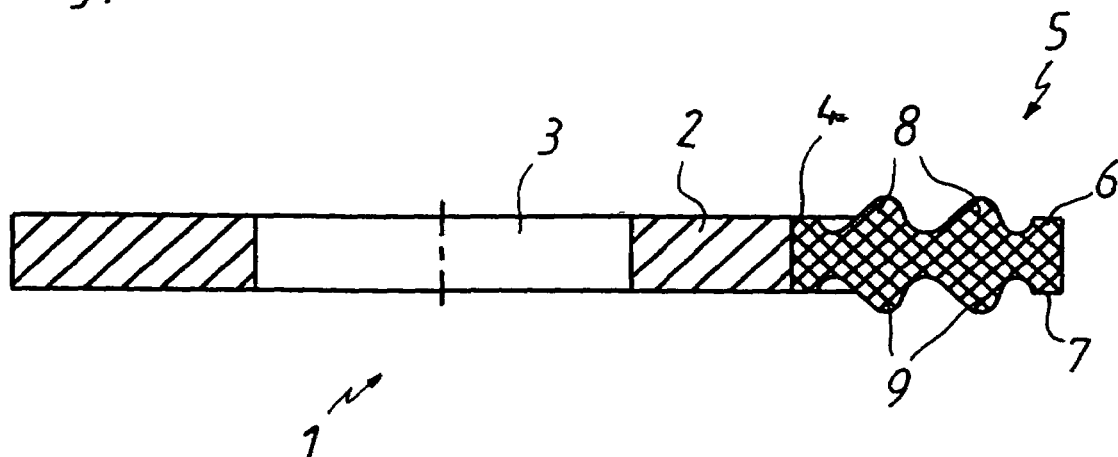
FIGS. 1a to 1c illustrate elastomeric seal bodies of different configurations.

The seal body 1 comprises a flat gasket with a metallic base body 2 providing a recess 3 which acts as a pass-through hole for the necessary stud-bolts.

The seal body 1 shown in this exemplary embodiment is of cylindrical cross section, with a seal element 5 being molded onto the outer perimeter surface 4 of the base body 2. The seal element includes undulating profiles 8, 9 on the area of both end surfaces 6, 7.

Figure 1B:
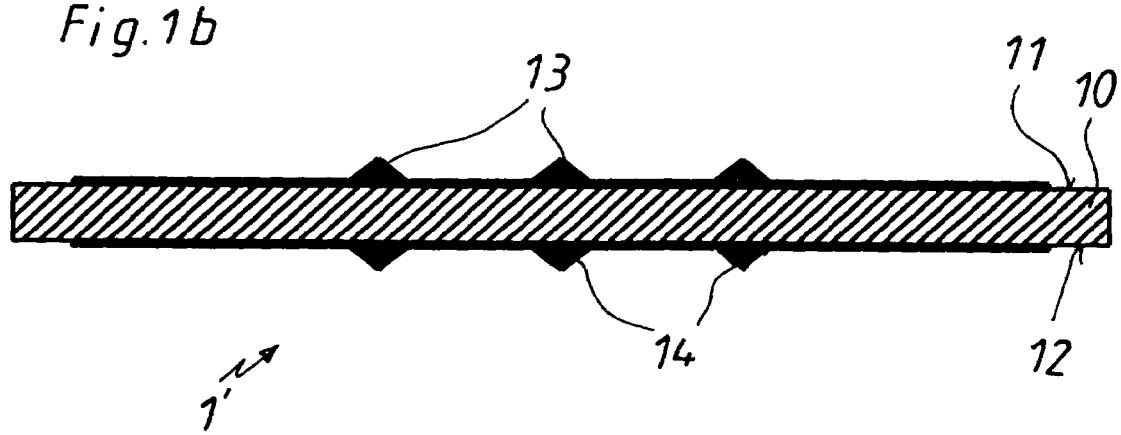

The seal body 1', as shown in FIG. 1b, comprises a metallic base body 10 onto which in the area of both end surfaces 11, 12 beads 13, 14 have been molded to create seal lips. The seal body shown is also of cylindrical cross section but does not include any recesses.

Figure 1C:
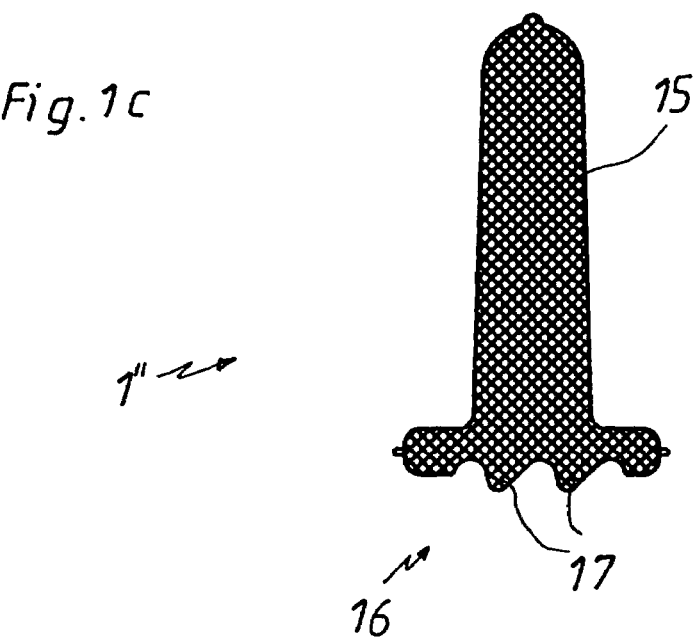

FIG. 1c shows a seal body 1" made of silicon material comprising an appendage 15 by means of which it can be introduced into a groove not shown here of a receiving body not shown here. Beads 17 have been molded on the seal area 16.

Figure 2A:
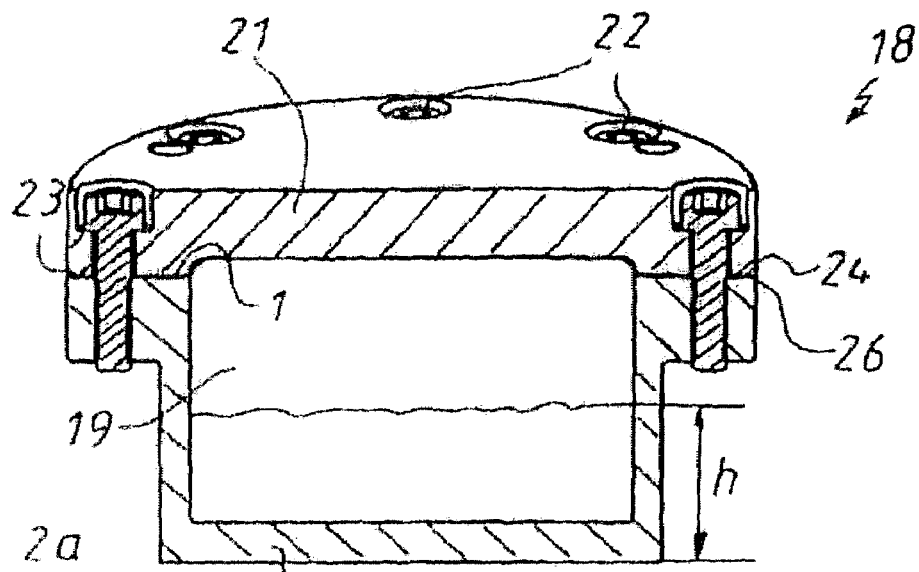
FIGS. 2a to 2c illustrate a testing device comprising seal bodies incorporated therein, in accordance with FIGS. 1a to 1c.
Figure 2B:
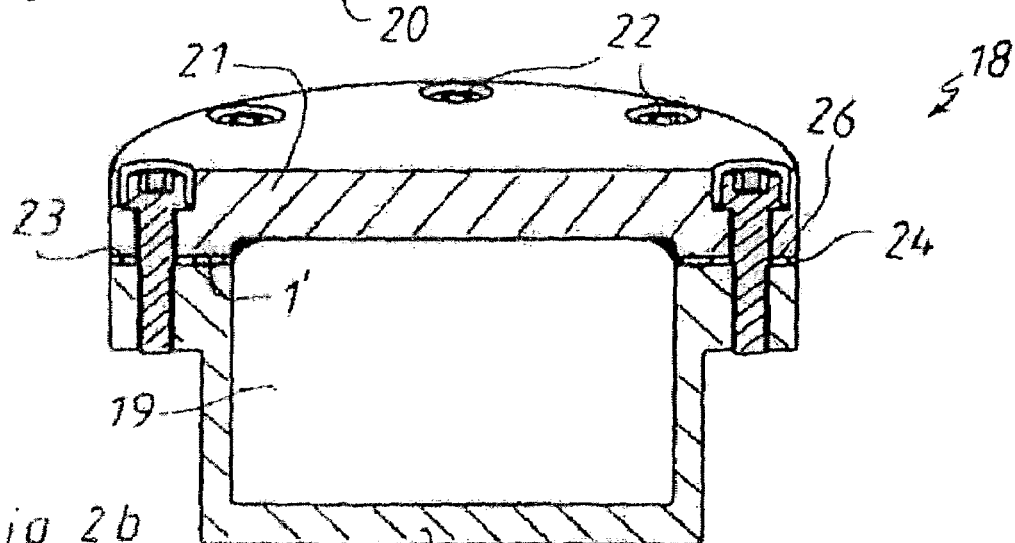
Figure 2C:
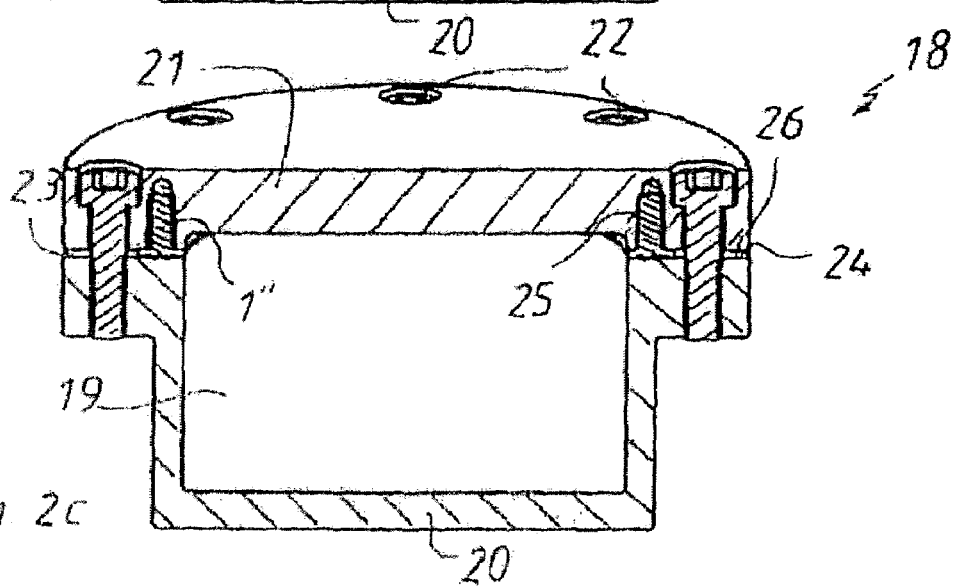

FIGS. 2a to 2c show the device 18, according to the invention, comprising the same component parts, namely a container 20, including a recess 19, and a corresponding lid 21, completely covering and closing off the recess 19. The connection between the container 20 and the lid 21 is provided by embedded socket screws 22. The respective seal body 1, 1', 1" is seated externally of the recess 19 in the area between the two opposing faces 23, 24, one belonging to the container 20, the other belonging to the lid 21. In the exemplary embodiment the faces 23, 24 are planar, as shown in FIG. 2a. The same applies to the face surfaces 23, 24 shown in FIG. 2b. The individual surfaces correspond to the surfaces of the respective seal body 1, 1' in the actual installation condition.

On the lid side a circular groove 25 has been provided to accommodate the seal body 1", as shown in FIG. 2c, where the appendage 15 of the seal body 1" is incorporated. The remaining surface parts of the face surface 24 as well as the entire area of the face surface 23 are also planar, whereby the surface of the individual face surface 23, 24 is also realistically configured.

Tightening of the screws 22 elastically deforms the respective seal body 1, 1' or 1" in the corresponding way, leaving a seal gap 26 between the container 20 and the lid 21, which is determined by the remaining material thickness of the seal body 1, 1', 1", the height of said gap being dependent on the pre-load used. A test medium is situated in the recess 19, in the present case a regular fuel mixture that can fill the container 20 up to the height h. Contrary to prior art no samples with reduced thickness are being used but, instead, seal bodies 1, 1' or 1" accordant to the actual operating conditions are analyzed, whereby the test medium, as it cannot escape upwards, must pass through the seal gap 26 and the seal body 1, 1', 1" provided therein. It is therefore possible to examine the permeation of a test medium through the respective seal body 1, 1', 1" under conditions representing real operation conditions, thus providing important information relevant for the development of new sealing systems. The device 18 can be placed in a temperature chamber, if required, to simulate the real application conditions as, for example, encountered in an internal combustion engine or in an exhaust system.

Because the particular seal body 1, 1', 1" is clamped between the face surfaces 23, 24 to its full extent, no component parts such as support screens or others are required.

The invention claimed is:

1. Device for measuring the permeability of a fluid and/or vapor test medium through an annular seal gap and elastomeric seal bodies spanning the seal gap comprising: a container incorporating a recess for containing the test medium, the recess being completely covered and closed off by an imperforate lid by way of screws fastening the lid to the container, wherein the seal body is positionable between surfaces of an end face of the container and a face of the lid, both surfaces being placed opposed to each other to define said annular seal gap providing an escape path for the test medium, and lockable in position by way of the screws using a predetermined load force, and the test medium being measurable as said medium escapes to the exterior through the remaining material thickness of the seal body through said seal gap between the surfaces.

2. Device as claimed in claim 1, wherein at least one of the surfaces is constructed with a non-planar contour.

3. Device as claimed in claim 1, wherein at least one of the surfaces has a groove corresponding to an installed condition in an operating state of the seal body.

4. Device as claimed in claim 1, wherein the screws comprise hexagon socket-type screws, in length not exceeding the outer border edge of the lid when the seal body is in the locked condition.

5. Device as claimed in claim 1, wherein the test of the permeability of a fluid and/or a vapor and/or gases through the seal gap is carried out by qualitative measurement of the weight reduction of the test medium.

6. Device as claimed in claim 1, wherein the surfaces of the respective faces correspond in contour and roughness to the face surface of the seal body in its installation state.

7. Device as claimed in claim 1, wherein the container and/or the lid are constructed of aluminum material.

8. Device as claimed in claim 1, wherein the container and/or the lid are constructed of synthetic material.

9. Device as claimed in claim 1, wherein the container and/or the lid are of cylindrical section.

10. Device as claimed in claim 1, wherein the measurement of permeability of a fluid and/or vapor and/or gases takes place under the influence of temperature.

11. A method for testing the permeability of an elastomeric seal body while compressed between opposite sealing surfaces under a predetermined load, the method comprising the steps of:

providing a container having a recess and an upper annular sealing face;

providing a lid having a lower annular sealing face and being constructed to completely close off the recess;

disposing a test medium in the recess;

disposing the seal body between the upper and lower annular sealing faces;

fastening the lid to the container under a predetermined load and completely closing off the recess by elastically compressing the seal body between the upper and lower annular sealing faces and defining an annular seal gap between the upper and lower annular sealing faces providing an escape path for the test medium; and measuring the escape of the test medium as it escapes through the seal gap and through the seal body.

12. The method of claim 11 further including providing the upper and lower annular faces as substantially planar surfaces.

13. The method of claim 11 further including providing the seal body with an annular upstanding appendage and at least one of the upper and lower surfaces with an annular groove and disposing the appendage in the groove during the disposing step.

14. The method of claim 11 further including heating the container, lid and seal body to simulate an actual sealing environment during the measuring step.

15. The method of claim 11 further including providing the lid with an imperforate surface sized to completely close off the recess in the container during the fastening step.

16. The method of claim 15 further including providing at least one of the lid and container as a synthetic material.

17. The method of claim 15 further including providing at least one of the lid and container as aluminum.

18. A seal permeability measuring assembly for measuring the permeability of a fluid and/or vapor test medium, comprising:

a container having a recess and an upper annular sealing face;

the test medium disposed in said recess;

a lid having a lower annular sealing face adapted to overlie said upper sealing face to define an annular seal gap between said faces and to completely close off said recess;

an elastomeric seal body elastically compressed in said seal gap between said upper and lower sealing faces; and a measuring device in communication with said assembly to measure said test medium as said test medium escapes through said seal gap.

19. The seal permeability measuring assembly of claim 18 wherein the lid has an imperforate surface sized to completely close off the recess.

20. The seal permeability measuring assembly of claim 19 wherein said seal body has an annular appendage and at least one of said upper and lower sealing faces has an annular groove for receipt of said annular appendage.

* * * * *